United States Patent [19]

Wenke et al.

[11] Patent Number: 5,584,889
[45] Date of Patent: Dec. 17, 1996

[54] OXIDATIVE HAIR DYEING PROCESS WITH DIHYDROXYBENZENES AND AMINOETHANETHIOLS

[75] Inventors: Gottfried Wenke, Woodbridge, Conn.; Guiseppe Prota, Naples, Italy

[73] Assignee: Clairol Incorporated, Stamford, Conn.

[21] Appl. No.: 351,794

[22] Filed: Dec. 12, 1994

Related U.S. Application Data

[63] Continuation-in-part of Ser. No. 174,488, Dec. 27, 1993, abandoned.

[51] Int. Cl.⁶ ..................... A61K 7/13
[52] U.S. Cl. ............. 8/424; 8/406; 8/407; 8/408; 8/587
[58] Field of Search ................. 8/405, 406, 407, 8/408, 424, 429, 587

[56] References Cited

U.S. PATENT DOCUMENTS

| | | | |
|---|---|---|---|
| 2,944,869 | 7/1960 | Kalopissis et al. | 8/11 |
| 4,268,264 | 5/1981 | Grollier et al. | 8/406 |
| 4,295,848 | 10/1981 | Grollier et al. | 8/410 |
| 4,479,803 | 10/1984 | Bachmann et al. | 8/406 |
| 4,746,322 | 5/1988 | Herlihy | 8/406 |
| 4,904,274 | 2/1990 | Schultz et al. | 8/406 |
| 5,131,911 | 7/1992 | Lang et al. | 8/406 |

*Primary Examiner*—Christine Skane
*Assistant Examiner*—Caroline L. Dusheck
*Attorney, Agent, or Firm*—Charles J. Zeller

[57] ABSTRACT

A process of dyeing hair by preparing and applying to the hair an aqueous reaction medium comprising an aminoethanethiol, a dihydroxybenzene and a ferricyanide or persulfate oxidizing agent, the composition optionally containing a color modifier selected from the group consisting of direct dyes, primary intermediates, couplers and mixtures thereof, and also containing a buffer to maintain the pH in the range from 2 to 11 during the oxidation reaction, and removing the aqueous reaction medium from the hair after the desired color is attained, and compositions and kits for practicing such processes.

38 Claims, No Drawings

1

OXIDATIVE HAIR DYEING PROCESS WITH DIHYDROXYBENZENES AND AMINOETHANETHIOLS

This application is a continuation-in-part of U.S. Ser. No. 08/174,488 filed Dec. 27, 1993, now abandoned.

FIELD OF THE INVENTION

This invention relates to compositions, methods and kits for dyeing hair. More specifically, the invention relates to methods of dyeing hair in which mixtures of certain dihydroxybenzenes and aminoethanethiols are oxidized to produce phaeomelanin, phaeomelanin-like, trichochrome and trichochrome-like pigments for coloring human hair. The invention relates also to compositions for conducting the hair dyeing process and to the packaged reactants sold in the form of a kit.

BACKGROUND OF THE INVENTION

Modern hair dyeing has developed from its initiation in the 1950's to the point where, today, it is the third largest product type in the hair category following shampoos and conditioners.

A wide variety of hair dyes or colorants have been developed, many of which involve oxidation of selected organic compounds or combinations of such compounds with oxidizing agents such as hydrogen peroxide. Other known oxidizing agents for use with such compounds include perborates, persulfates and perhalites, particularly periodates. These oxidizing agents are generally employed as ammonium salts or as salts of alkali metals. In the course of this development, it has been learned that the applicability of an oxidant to one or more oxidizable substrates does not permit the prediction that the same oxidant or apparently similar oxidant will be useful for oxidizing another oxidizable substate to achieve a desirable color change in human hair.

Despite the large number of hair dyeing compositions and processes which have been developed, the art is constantly searching for methods and compositions to improve the efficiency of the hair coloring process, decrease the time required, impart desirable tints and tones to the hair and avoid and use of hydrogen peroxide, which may be damaging to hair or skin.

PRIOR ART

U.S. Pat. No. 4,746,322 to Herlihy describes hair coloring procedures in which hair is colored by oxidation of 3,4-dihydroxyphenylalanine (dopa) or its derivatives by an iodate or periodate oxidant (possibly in admixture with a persulfate) and in the presence of selected dispersing agents.

BRIEF SUMMARY OF THE INVENTION

In the process of the present invention human hair is dyed to attain desirable permanent tints and tones by applying to the hair selected aminoethanethiols and selected dihydroxybenzenes together with an oxidizing agent selected from the group consisting of persulfates and ferricyanides contained in one or more aqueous compositions. The hair is dyed at a pH of from about 2 to about 11, preferably from about 5 to about 9. The dihydroxybenzenes employed in the invention are o- and p-dihydroxybenzenes, which may be further substituted as described below.

Among the important advantages achieved by the practice of this invention is that the oxidative development of color is accomplished without the use of hydrogen peroxide, thereby avoiding the known disadvantages of this oxidizing agent. Another advantage is that at least some of the end products of the oxidation reaction are expected to be identical to or closely related to trichochromes or phaeomelanins, which are the natural red and yellow pigments present in hair. Thus, by the practice of this invention it is possible to achieve natural looking red and yellow hair tones that have heretofore eluded the art.

The reactants employed in this invention are all well known or can be produced by well known procedures.

DETAILED DESCRIPTION OF THE INVENTION

The hair dyeing process of the present invention comprises applying to the hair an aqueous system comprising one or more aqueous compositions with a view toward reacting aminoethanethiol with a dihydroxybenzene together with an oxidizing agent selected from the group consisting of persulfates, ferricyanides and mixtures thereof, within a pH ranging from about 2 to about 11, preferably from about 5 to about 9. The application to the hair is in such manner that sufficient oxidation takes place within the hair shaft to provide a tinctorially effective amount of hair coloring pigments to permanently color the hair. These pigments are believed to be related to natural phaeomelanin and trichochrome pigments, as hereinafter explained. It is believed that intermediates to the melanin and melanin-like pigments obtained in the process diffuse into the hair shaft during the period of contact with the formation of the pigment occurring in the hair shaft rather than on the hair. As a result the hair is colored permanently and does not wash out by repeated shampooing. The total time of the process during which composition is applied and left in contact with the hair is normally less than one hour, typically from about 5 to 50 minutes, preferably 5 to 20 minutes.

"Hair dye composition" means an aqueous composition containing the aminoethanethiol and dihydroxybenzene reactants in tinctorially effective concentrations to impart a coloration to the hair in accordance with the process of the present invention. In the "one step" process described below the hair dye composition further contains an amount of the primary oxidizing agent to effect the quinone-forming reactions hereinafter described. In the "two step" process all or a portion of the primary oxidizing agent is provided in a separate aqueous composition for application to the hair following treatment of the hair with the hair dye composition.

"Primary oxidizing agent" means the ferricyanide and persulfate oxidizing agents.

"Post-treatment composition" means an aqueous composition containing an oxidant optionally applied to the hair following the application of the hair dye composition in the one step process or following the second step oxidative treatment in the two-step process. The oxidant used in the post-treatment step may be a primary oxidizing agent or may be another oxidizing agent as indicated below.

By "permanent" is meant a color not removable by shampooing with a conventional surfactant-containing shampoo, the permanency being attributable to the inability of the formed pigments to diffuse from the hair shaft in view of their molecular sizes.

By "applying" is meant contacting the hair to be dyed with the hair dye composition together with the primary oxidizing agent including any oxidant contained in the post-treatment composition. Thus, the primary oxidizing agent may be applied with the hair dye composition or as one or more separate treatment compositions, in an amount sufficient to effect a color change of the hair. The hair dye composition may be prepared just prior to contact with the hair or may be formed on the hair.

Trichochromes are yellow and red polycyclic pigments of defined chemical structure, several of which have been extracted from red hair and feathers under alkaline conditions.

Phaeomelanins are reddish-brown nitrogen and sulfur containing macromolecular pigments found in phaeomelanocytes. Phaeomelanins are derived from tyrosinase oxidation of tyrosine and subsequent reaction with cysteine.

All percents by weight defined in this specification and claims are percents by weight based on the total weight of the composition.

It is the object of this invention to provide a process and composition that leads to the formation phaeomelanin, trichochrome and related pigments. The reactions that are believed to take place are complex, with many of the reactions occurring outside the biosynthetic pathway. These reactions are believed to produce compounds analogous to the phaeomelanin and trichochrome pigments that are biosynthetically produced, and are hereinafter referred to as phaeomelanin-like and trichochrome-like pigments. Moreover, these definitions are intended to include any reaction products as may be formed by reaction of a direct dye, primary intermediate or coupler with the dihydroxybenzenes or reaction intermediates thereof, under the oxidative conditions existing in the practice of the present invention. It is believed that these terms and their meanings are well understood by the skilled artisan even though the exact chemical identity of some of the products, particularly those formed by reaction of the intermediates formed during the oxidative process with a direct dye, primary intermediate and/or coupler in accordance with the present invention is not precisely known or understood.

Dihydroxybenzenes useful in the practice of the present invention are represented by Formulas I and II below:

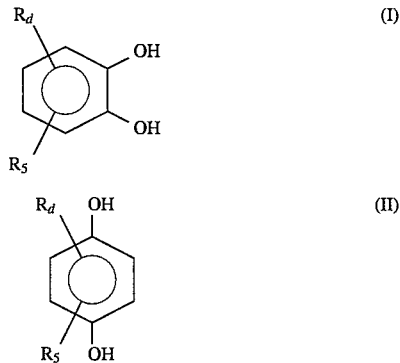

and the aminoethanethiols used herein are represented by the Formula III:

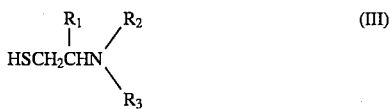

wherein

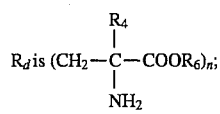

$R_2$, $R_3$, $R_4$ and $R_5$, which may be the same or different, are H, $C_1$–$C_6$ alkyl or $C_1$–$C_6$ hydroxyalkyl; $R_1$ is H or $COOR_7$; $R_6$ and $R_7$, which may be the same or different, are alkali metal, H or $C_1$–$C_6$ alkyl, and n is 0 or 1.

The tinctorially effective amounts of the dihydroxybenzene and aminoethanethiol compounds depend upon many factors that can be readily evaluated by the skilled artisan either from experience or from a few tests. These factors include, for example, the color desired, the selected coloring agent or agents, the original color of the hair to be treated, the pH, auxiliary coloring agents employed, etc. Typically, however, the hair dye composition of the invention will contain from about 0.1 to 10% by weight of each of the dihydroxybenzene and the aminoethanethiol compounds, preferably 0.1 to 2%. When $R_d$ is hydrogen (i.e. n=0) the aminoethanethiol and dihydroxybenzene components are generally present in the hair dye composition in approximately equimolar amounts, with a slight excess, typically not greater than about 15%, of the aminoethanethiol being present to account for side reactions. When $R_d$ is $CH_2C(R_3)(NH_2)COOR_6$ (i.e., n=1) the possibility exists for competing reactions leading to the formation of other chromophoric compounds, e.g., indoles when the dihydroxybenzene is a catechol. It has been found, however, that such reactions are suppressed by using a molar excess of the aminoethanethiol component relative to the dihydroxybenzene. In such instance a mole ration of aminoethanethiol to dihydroxybenzene of up to about 4:1 is acceptable, with a ratio of up to 2:1 being preferred.

In some instances, however, it may be desirable to form such chromophoric compounds (e.g., dihydroxyindoles and the resulting eumelanins), along with the pigments of the present invention. In such instances the molar ratio of the aminoethanethiol to the dihydroxybenzene may be as low as 1:2. Thus, the aminoethanethiol to dihydroxybenzene mole ratio can vary from about 1:2 to 4:1, especially about 1:1 to about 2:1. In some instances other reactants, e.g., a coupler, may react with the dihydroxybenzene reactants.

The preferred dihydroxybenzenes are dopa species, i.e., compounds of Formula I in which n=1, as such compounds appear to most closely mimic the biosynthetic melanin pathway. The dopa species are dopa, alpha alkyl dopa having 1 to 4, preferably 1 to 2, carbons in the alkyl group, and dopa alkyl esters having 1 to 6, preferably 1 to 2, carbons in the alkyl group. Dopa is especially preferred. When n=0, the preferred compounds are catechols and paradihydroxybenzenes in which $R_5$ is H, $C_1$ to $C_2$ alkyl or $C_1$ to $C_2$ hydroxyalkyl, with the catechols thereof being especially preferred, in particular 4-methylcatechol and hydroquinone. Of the aminoethanethiols, cysteine and aminoethanethiol are especially preferred.

The primary oxidizing agents employed in this invention may be selected from persulfate and ferricyanide oxidizing agents, including ammonium salts and salts of alkali metals, preferably sodium or potassium. The presently preferred oxidizing agents are the easily soluble sodium persulfate and potassium ferricyanide salts. It is applicants' discovery that the persulfate and ferricyanide oxidizing agents uniquely enable the formation and subsequent reaction of intermediates leading to the phaeomelanin, phaeomelanin-like, trichochrome and trichochrome-like pigments of the present invention. Thus, applicants provide a hair dyeing process in which the dihydroxybenzene is first oxidized to form a quinone, the quinone then being substituted via a nucleophilic addition with the aminoethanethiol, followed by further oxidation to the corresponding thio-substituted quinone. This is followed by ring closure to form dihydrobenzothiazines. The ring closure reactions believed to take place after the initial substitution of the aminoethanethiol group onto the phenyl nucleus are:

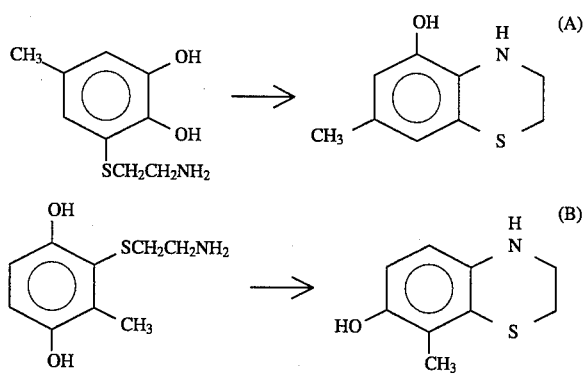

Ring closure is followed by oxidative conversion of the resultant 1,4-dihydrobenzothiazines to the coloring pigments of this invention. The proposed reaction sequence does not, however, preclude the possibility that more than one aminoethanethiol substituent is added to the benzene ring and subsequent oxidation follows a different route. Accordingly, a slight molar excess of the aminoethanethiol, based on the substitution of only one aminoethanethiol group, is normally employed.

It is seen that three oxidation steps take place in the sequence of reactions leading to the formation of the hair dye pigments of this invention. The last oxidation step, namely, the conversion of the benzothiazines to the pigments, may take place slowly using oxygen in the air, but preferably will be accelerated by using an oxidant. For this conversion a variety of oxidants is suitable. Mention may be made of the ferricyanide and persulfate primary oxidizing agents, as well as chlorite, periodate, iodate, permanganate, acidic nitrite, dichromate and other oxidants generally deemed useful in the hair dyeing art. A low strength hydrogen peroxide may also be used in a solution having a pH of from about 7 to about 8.5. While useful, peroxide in high strength and at high pH is an excessively powerful oxidant, and may tend to bleach the dyed hair. Of course, higher strength peroxide solutions are useful as a post-treatment to lighten dyed hair. Generally, ferricyanide has been found to be less useful as a post oxidant treatment.

In effecting the first two oxidations, namely, the quinone-forming reactions, the primary oxidizing agent is used. The amount of this oxidizing agent for such purpose will generally be a stoichiometrically equivalent amount. Since each quinone-forming reaction involves a two electron transfer and because ferricyanide can transfer only one electron, two moles ferricyanide are needed per mole of dihydroxybenzene for each quinone-forming reaction, or a total of four moles ferricyanide, which is its stoichiometrically equivalent amount. In the case of persulfate, two electrons can be transferred. Accordingly, two moles of persulfate are required per mole of dihydroxybenzene as its stoichiometric equivalent amount. In view of the reaction kinetics, however, the primary oxidizing agent may be present in an excess over the aforementioned theoretical amounts, especially in the case of persulfate. Typically, the amount of ferricyanide or persulfate oxidizing agent used in the practice of the process is less than a 50% excess over its respective stoichiometric equivalent amount.

The primary oxidizing agent is present in the hair dye composition or in a second step treatment composition in a concentration of from about 0.5 to about 30% preferably from about 1 to about 15%, in the case of persulfate, and in a concentration of from about 0.5 to about 15%, preferably from about 1 to about 10%, in the case of ferricyanide. The persulfate and ferricyanide oxidizing agents may be used individually or mixed, or may be used in separate steps of the process.

Inasmuch as the pH of the reaction medium will vary during the reaction, it is desirable to provide a sufficient amount of a pH control agent in the reaction medium to maintain the pH between about 2 to about 11, preferably from about 5 to about 9. In the process of the present invention, the preferred pH depends on the primary oxidizing agent used and on the dyeing procedure (one-step dyeing or two-step dyeing). Thus, persulfates are usually optimal at alkaline pH, and ferricyanide is used preferably at a pH of 6 to 11, most preferably 7 to 9. The first step of the two step process if preferably conducted at high pH to maximize penetration of the hair dye components into the hair.

Reagents for the control of pH in the compositions of this invention include various conventional buffers including those based on inorganic salts such as carbonates and bicarbonates, as well as aminic buffers such as TRIS. The pH control agents also include organic compounds widely employed in hair colorant compositions to maintain the desired pH. These include, for example, fatty acids, especially long chain monocarboxylic or dicarboxylic acids such as dimer acid, linoleic acid or stearic acid, in combination with amines such as ammonia, 2-amino-2-methyl propanol and monoethanolamine. Both types of reagents are referred to herein and in the appended claims as pH control agents.

In the hair dyeing process of this invention the aminoethanethiol and the dihydroxybenzene reactants are applied to the hair in an aqueous hair dye composition in the presence of the selected primary oxidizing agent, and are maintained in contact with the hair for a sufficient period of time for a tinctorially effective amount of pigment to form. The "contact" time as that term is employed herein is the period of time from the mixing of the reactants to the removal from the hair.

The pigment should form in the hair shaft so that it elicits a permanent color change. It is believed that the dihydroxybenzene and aminoethanethiol molecules and the intermediates formed in the course of the oxidative sequence are sufficiently small so that they will diffuse into the hair strand along with the oxidizing agent and the aqueous carrier. The trichochromes, phaeomelamins and analogous pigments that form within the hair shaft, however, are such large molecules that they become trapped within the hair, thereby imparting permanency to the color. It will be apparent that applying the hair dye composition to the hair after an appreciable amount of oxidation has taken place is not suitable since the pigments will form on the surface of the hair and not in the hair, and will be largely stripped away during subsequent shampooing.

The process of the present invention can be practiced in several embodiments to achieve the desired results.

In the "one step" or "simultaneous" procedure, the aqueous hair dye composition comprises the aminoethanethiol and the aqueous dihydroxybenzene reactants as well as the primary oxidizing agent at the requisite pH. This hair dye composition is applied to the hair and is maintained in contact with the hair to be treated until a tinctorially effective amount of pigment is formed in the hair to effect the desired result. The oxidation of the benzothiazine intermediates to the pigments of the present invention may be accomplished slowly by using oxygen in the air as the oxidizing agent or most preferably may be conducted by the post- oxidation step hereafter described. The hair is then rinsed and dried.

When ferricyanide is the sole primary oxidizing agent in the one step process, it is present in the hair dye composition in about a stoichiometric equivalent amount, or in slight excess, usually not more than 15%, over that amount, and it is usually desirable to conduct a post-treatment in which an oxidant different from the ferricyanide oxidizing agent is applied to the hair to effect conversion of the benzothiazines to the pigments of the present invention. When persulfate is the sole primary oxidizing agent, excess of the persulfate over its stoichiometric equivalent amount is preferably incorporated as set forth above. Moreover, sufficient excess may be incorporated in the hair dye composition so as to satisfy the requirements of the benzothiazine oxidation. Alternately, the post-oxidative step may be used.

In the "two step" or "sequential process", the aqueous hair dye composition comprises the aminoethanethiol and the dihydroxybenzene, which composition is applied to the hair for a period of from about 1 to about 30 minutes to permit these reactants to diffuse into the hair strand. An aqueous solution containing the primary oxidizing agent is then brought into contact with the hair for an additional 1 to 20 minutes, preferably 2 to 10 minutes, until the desired coloration is attained. The hair is then rinsed and dried. The primary oxidizing agent is present in the aqueous solution at a concentration as previously described. The primary oxidizing agent stoichiometric requirements are analogous to the one step process, and the benzothiazine intermediates may be converted to the pigments of the present invention via air oxidation, with an oxidative post-treatment composition, or using primary oxidizing agent present in excess in the aqueous solution. It is noted that the primary oxidizing agent solution is different from the oxidative post-treatment composition because only the selected primary oxidizing agents effect the formation of the quinones in amounts sufficient to generate tinctorially effective pigment concentrations.

In a variation of this two step process, the hair dye composition comprises the aminoethanethiol and the dihydroxybenzene reactants along with a portion of the stoichiometric equivalent amount of the primary oxidizing agent. This hair dye composition is applied to the hair and is maintained in contact with the hair so that some oxidation takes place, with the reaction products diffusing into the hair strand along with the original reactants. Oxidation of these reaction products as well as conversion of residual unreacted reactants will be completed in the second step. The primary oxidizing agent selected for the first step can be the same or different in the second step.

In one embodiment of the two step process, ferricyanide is incorporated in the hair dye composition in an amount of about one half of its stoichiometric equivalent amount. Inasmuch as ferricyanide is especially reactive to the dihydroxybenzene, the conversion of the dihydroxybenzene to the quinone followed by the nucleophilic addition of the aminoethanethiol is rapid and substantially complete. In the second step persulfate is incorporated in the aqueous oxidizing agent solution in an amount of about one half of its stoichiometric equivalent amount plus the desired excess as hereinbefore described. The second step completes the conversion to the benzothiazine, and depending on the amount of persulfate in excess of the one half stoichiometric equivalent amount, will complete the oxidation to the pigments. The concentrations of the primary oxidizing agents in the hair dye composition and the oxidizing agent solution are the same as set forth above. Of course, the amount of primary oxidizing agent can be proportioned between the hair dye composition and the oxidizing agent solution as desired, provided sufficient oxidizing agent is used to effect the formation of the quinones.

As indicated above, the hair treated in the one step or the two step processes may be subjected to a post-treatment with an oxidant solution. This post-treatment composition is usually employed following the one step procedure, especially when the primary oxidizing agent used in the one step procedure is a ferricyanide. The purpose of the oxidative post-treatment is to complete the conversion of the various intermediate chemical species present in the aqueous reaction medium at this stage in the process including especially the benzothiazines as well as other immediate melanin precursors to the pigments of the present invention. The degree to which completion is required depends upon the amount of primary oxidizing agent in excess of the stoichiometric equivalent amount used in the practice of the one step or the two step processes, as described above. Thus, the oxidative post-treatment can be used to effect essentially all of the conversion of the benzothiazines to pigments, or may be used to merely complete the conversion of residual pigment precursors into the useful pigments of this invention. In this regard it should be understood that the phaeomelanin, trichochrome and analogous pigments obtained by the process of the present invention are the dimer, trimer and higher oligomer reactive products obtained from benzothiazine. It is believed that the benefit of the oxidative post-treatment lies in assisting in the conversion to the more highly colored and higher molecular weight pigment species, resulting in deeper colors. Generally, the oxidative post-treatment composition is applied to the hair following a rinse after completion of the one step or two step process.

As previously indicated, any conventional oxidizing agent generally used in oxidative hair dye processes can be employed as the oxidant in the oxidative post-treatment procedure. Suitable oxidants for this step are, for example, the alkali metal and ammonium salts of ferricyanides, persulfates, perborates, iodates, periodates, permanganates, dichromates, acidic nitrites, dilute hydrogen peroxide, chlorites, and compatible mixtures thereof. Persulfates and periodates are preferred. Periodates are especially preferred. Ferricyanides are not preferred.

The oxidant solution used in the oxidative post-treatment typically contains from about 0.1 to about 30% by weight oxidant, and is applied to the hair in sufficient amount to ensure high yield of the pigments. The solution is generally provided in substantial excess, and is permitted to remain in contact with the hair for about 1 to 30 minutes, preferably 2 to 15 minutes. The pH of the solution is typically from about 4 to about 10, preferably from about 6 to about 9.

A further aspect of the present invention is the optional incorporation of a hair color modifier selected from the group consisting of direct dye, primary intermediate or coupler, and mixtures thereof in the reaction mixture. It is believed these components when present in the reaction mixture react at least in part with the intermediate compounds formed during the sequence of reactions leading to pigment production, thereby providing trichochrome-like and phaeomelanin-like compounds that impart additional chromatic characteristics to the pigments ultimately obtained. When such oxidizable color modifying compounds are employed, the amount of primary oxidizing agent in the reaction mixture is increased to provide for the oxidation of these materials since some of them will be directly oxidized in the usual way rather than reacting with an intermediate of the primary reaction sequence. It will be apparent to the skilled artisan that by use of these auxiliary coloring agents, a wide variety of tints, tones and shades can be achieved. As previously mentioned, the dopa species may under certain circumstances be considered to be color modifiers, in that oxidation to a dihydroxyindole can take place when sufficient primary oxidizing agent is present coupled with a deficit of the aminoethanethiol. The dihydroxyindoles are useful as they provide eumelanins, and can provide desired shades to the final hair color.

The concentration of hair color modifiers is normally less than about 10 mg/ml, and preferably is present in the reaction medium at from about 0.01 to about 5 mg/ml, most preferably from about 0.05 to about 2 mg/ml. The amount of these components should not be so great as to prevent the formation of the principal pigment. That is, the process of the present invention contemplates reaction of only a portion of the intermediate reaction products with the hair color modifiers.

A wide variety of direct dyes, primary intermediates and couplers are known to the skilled artisan and can be employed in this invention.

The presently preferred primary intermediates and couplers include:

| | |
|---|---|
| Primary Intermediates: | p-phenylenediamine |
| | p-aminophenol |
| | o-aminophenol |
| | N,N-bis(2-hydroxyethyl)-p-phenylenediamine |
| | 2,5-diaminopyridine |
| | p-toluenediamine |
| Couplers: | resorcinol |
| | m-aminophenol |
| | 1-naphthol |
| | 5-amino-o-cresol |
| | 2-methylresorcinol |
| | N-acetyl dopa |
| | 4,6-di(hydroxyethoxy)-m-phenylenediamine |
| | m-phenylenediamine |

Direct dyes which may be used in the invention include, for example, nitro dyes, azo dyes and anthraquinone dyes.

The variously described embodiments of the present invention may also include in the hair dye composition or in any of the oxidizing agent-containing solutions including the post-treatment solution one or more optional ingredients. Such ingredients include well-known conventional additives usually employed in oxidative hair coloring compositions such as organic solvents, thickeners, surface-active agents to enhance diffusion of the dyeing agents into the hair shaft, pH adjusting agents, antioxidants, fragrances and chelating agents.

Surface-active agents employed in the dyeing compositions of this invention can be anionic, nonionic, cationic, amphoteric or zwitterionic. By way of examples of the various types of surface-active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides; salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glycerol monostearate; triethanolamine oleate; sodium salt of palmitic methyl taurine; cetyl pyridinium chloride; lauryl sulfonate; myristyl sulfonate; lauric diethanolamide; polyoxyethylene stearate; ethoxylated oleyl diethanolamide; polyethylene glycol amides of hydrogenated tallow; stearyldimetnyi benzyl ammonium chloride; dodecylbenzene sodium sulfonate; triethanolamine salt of p-dodecylbenzene sulfonate; nonylnaphthalene sodium sulfonate; dioctyl sodium sulfonsuccinate; sodium N-methyl-N-oleyl taurate; oleic acid ester of sodium isethionate; sodium dodecyl sulfate; the sodium salt of 3-diethyl tridecanol-6-sulfate and the like. The quantity of surface-active agent can vary over a wide range, such as from about 0.05% to 15% and preferably from about 0.10 to 5% by weight of the composition, The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

Chelating and sequestering agents include, for example, ethylenediaminetetraacetic acid, sodium citrate, etc., and may be present in an amount of under about 1%.

A thickening agent may also be incorporated in the dyeing composition of this invention, which may be one or several of those commonly used in hair dyeing. These are exemplified by such products as sodium alginate, gum arabic, cellulose derivatives such as methylcellulose (e.g., Methocel 60HG), the sodium salt of carboxymethylcellulose, hydroxyethyl-cellulose (e.g., Cellosize QP-40), acrylic polymers such as polyacrylic acid sodium salt, and inorganic thickeners such as bentonite. The quantity of the thickening agent can also vary over a wide range, even as high as 20%. Ordinarily it will range from about 0.1 to 5% by weight of the composition. The viscosity of the composition may vary from about 1 cp to about 100,00 cps. For a typical lotion formulation, composition viscosity is between about 100 cps to about 10,000 cps, at which viscosity the composition can be applied to the hair without running or dripping.

The list of optional ingredients is not intended as limiting. Other suitable adjuvants for inclusion in the hair dye composition or in the oxidant solutions are recited, for example, in Zviak, *The Science of Hair Care* (1986) and Balsam and Sagarin, *Cosmetics: Science and Technology*, Vol. 2 (Second Edition 1972).

The process of the present invention may conveniently be practiced by providing premeasured amounts of the reactants in separate containers packaged in kit form. The user simply admixes the reactants for application to the hair in accordance with the selected practice of the invention. It will be apparent that no special expertise is required to carry out the process, and accordingly the product and process are equally suitable for in-home use by the nonprofessional as well as salon use by the professional. Advantageously, the product in kit form is shelf-stable and is therefore suitable for retail sale and without precautions required for some hair colorant compositions, e.g., storage under anaerobic conditions.

The kit provided in accordance with this aspect of the invention comprises hair colorant precursor, a first container containing the oxidizable colorant mixture and a second container containing the oxidant. The buffer may be individually packaged in a third container or may be present in the first or second container. Selected modifiers may be mixed with the basic hair colorant of the invention or may be in a separate container. Of course, the dihydroxybenzene and the aminoethanethiol may be in separate containers, but it is presently preferred that they be in the same container.

While the kit may include packets containing amounts, preferably premeasured, of dry powders for preparation of these solutions, it is more convenient to provide them as solutions. Moreover, solutions containing premeasured quantities of the constituents facilitates their correct use by the consumer.

One or more additional containers containing the optional constituents may be provided in the kit. The optional constituents may also be contained within the solutions of the previously described containers, barring any incompatibility.

The consumer admixes the components of the kit, suitably as the aqueous solutions or as dry powders and water, according to written instructions, to obtain the aqueous compositions for application to the hair. Mixing may be conducted in a separate vessel supplied with or external to the kit, or may take place in a container of the kit adapted to provide sufficient head space for mixing. The reactants may also be admixed on the hair of the user. Reaction commences upon combining the oxidizing agent with the dehydroxybenzene and aminoethanethiol reactants. The hair dye component will subsequently oxidize as described herein whereby a permanent hair color is obtained. After the desired hair shade is reached, most preferably within about 30 minutes, the hair dye composition that was applied to the hair is removed, preferably with a conventional shampoo.

In the examples which follow, the hair coloring effects achieved with the process of this invention are evaluated utilizing the standard Hunter Tristimulus values. In the Hunter method, the parameters a and b may be positive or negative and define the chromatic condition of the hair. Thus, the more positive the a value, the greater the redness of the hair, while a negative a value indicates greenness. Similarly, positive b values indicate yellowness, while negative b values indicate blueness. The L parameter is a measure of color intensity, and has a value of 0 for absolute black to 100 for absolute white. Generally, hair having an L value of about 15 or less is considered black, while an L value of about 60 is white. It should be understood that the L value scale is not linear, but rather is sigmoidal. Proximate to 0 and proximate to 100 hair color intensity apparent to the human eye varies minimally with unit changes in the L value. Between values of about 20 to about 50, hair color intensity varies significantly with unit changes in L value. Thus, the Hunter values are more sensitive in the region where the human eye is able to perceive color changes.

EXAMPLE 1

100 mg DOPA (0.5 mmole) and 61 mg cysteine (0.5 mmole) were dissolved in 10 ml of an aqueous solution of TRIS buffer (850 mg TRIS; 3.5 ml 1N HCl in 10 ml). 228 mg ammonium persulfate (1.0 mmole) were added and dissolved as fast as possible (by shaking). The solution (pH approx. 8.2) was applied to a tress of white hair and left for 20 minutes. The hair was briefly rinsed with water, shampooed and dried. Hunter measurements were made on the dyed hair and compared to the undyed hair as noted below:

|  | L | a | b |
|---|---|---|---|
| untreated hair: | 62.6 | 0.2 | 18.3 |
| treated hair: | 41.5 | −0.9 | 8.3 |

EXAMPLE 2

A tress of white hair was treated as in Example 1. After rinsing with water, the tress was exposed to an aqueous formulation, containing approx. 10% $(NH_4)_2S_2O_8$ for 4 minutes. Afterwards, the tress was rinsed with water, shampooed and dried. The Hunter values were:

|  | L | a | b |
|---|---|---|---|
| untreated hair: | 62.6 | 0.2 | 18.3 |
| treated hair: | 29.2 | 3.7 | 10.9 |

EXAMPLE 3

100 mg DOPA (0.5 mmole) and 121 mg cysteine (1.0 mmole) were dissolved in 10 ml of an aqueous solution of TRIS buffer (640 mg TRIS; 2.6 ml 1N HCl in 10 ml). 342 mg ammonium persulfate (1.5 mmole) were added and dissolved as fast as possible (by shaking). The solution (pH approx. 8.0) was applied to a tress of white hair and left for 20 minutes. The hair was briefly rinsed with water, shampooed and dried. The Hunter values were:

|  | L | a | b |
|---|---|---|---|
| untreated hair: | 62.6 | 0.2 | 18.3 |
| treated hair: | 38.4 | −0.9 | 6.7 |

EXAMPLE 4

100 mg DOPA (0.5 mmole) and 61 mg cysteine (0.5 mmole) were dissolved in 10 ml of an aqueous solution of TRIS buffer (640 mg TRIS; 2.6 ml 1N HCl in 10 ml). 659 mg potassium ferricyanide (2.0 mmole) were added and dissolved as fast as possible (by shaking). The solution (pH approx. 7.5) was applied to a tress of white hair and left for 20 minutes. After rinsing with water, the tress was exposed to an aqueous formulation containing approx. 10% $(NH_4)_2S_2O_8$ for 4 minutes. Afterwards, the tress was rinsed with water, shampooed and dried. The Hunter values were:

|  | L | a | b |
|---|---|---|---|
| untreated hair: | 62.6 | 0.2 | 18.3 |
| treated hair: | 14.5 | 0.6 | 1.3 |

EXAMPLE 5

100 mg DOPA (0.5 mmole) and 121 mg cysteine (1.0 mmole) were dissolved in 10 ml of an aqueous solution of TRIS buffer (640 mg TRIS; 2.6 ml 1N HCl in 10 ml). 659 mg potassium ferricyanide (2.0 mmole) were added and dissolved as fast as possible (by shaking). The solution (pH approx. 7.5) was applied to a tress of white hair and left for 20 minutes. After rinsing with water, the tress was exposed to an aqueous formulation, containing approx. 10% $(NH_4)_2S_2O_8$ for 4 minutes. Afterwards, the tress was rinsed with water, shampooed and dried. The Hunter values were:

|  | L | a | b |
|---|---|---|---|
| untreated hair: | 62.6 | 0.2 | 18.3 |
| treated hair: | 27.3 | 2.4 | 9.4 |

What is claimed is:
1. A method of permanently coloring hair to a desired color comprising the steps of:

(a) applying an aqueous system to the hair at a pH of from abut 2 to 11, the aqueous system comprising a tinctorially effective amount of (i) a dihydroxybenzene having a structure:

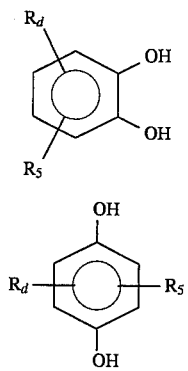

(ii) an aminoethanethiol having the formula

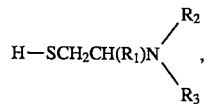

and (iii) a ferricyanide oxidizing agent, wherein

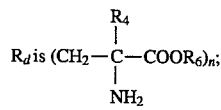

$R_1$ is H or $COOR_7$; $R_2$, $R_3$, $R_4$ and $R_5$, which may be the same or different, are H, $C_1$–$C_6$ alkyl or $C_1$–$C_6$ hydroxyalkyl; $R_6$ and $R_7$, which may be the same or different, are alkali metal, H or $C_1$–$C_6$ alkyl, and n is 1, the ferricyanide oxidizing agent being present in said aqueous system in at least about a stoichiometric equivalent amount relative to the dihydroxbenzene component (i), and (b) permanently coloring the hair by allowing the aqueous system to remain in contact with the hair for a period of time sufficient to achieve the desired color.

2. The method of claim 1 wherein the aqueous system comprises an aqueous hair dye composition containing the dihydroxybenzene and the aminoethanethiol hair dye components, each of which is present at a concentration of from about 0.1 to about 10% by weight of the hair dye composition.

3. The method of claim 2 wherein the hair dye composition further contains the ferricyanide oxidizing agent, said oxidizing agent being present in the hair dye composition at a concentration of from about 0.1 to 15%, the oxidizing agent being present in the hair dye composition in said stoichiometric equivalent amount.

4. The method of claim 3 wherein the ferricyanide oxidizing agent is potassium ferricyanide present in the hair dye composition in an amount that is less than about a 15% excess over its stoichiometric equivalent amount.

5. The method of claim 2 wherein the aqueous system further comprises an aqueous solution containing at least a portion of the ferricyanide oxidizing agent present in the system, said aqueous solution being applied to the hair following the application of the hair dye composition to the hair.

6. The method of claim 5 wherein the ferricyanide oxidizing agent is present in the aqueous system in an amount of from about a stoichiometric equivalent amount to about a 50% excess over such amount.

7. The method of claim 6 wherein the portion of the ferricyanide oxidizing agent not contained in the aqueous solution is present in the hair dye composition.

8. The method of claim 1, 3, or 6 wherein the mole ratio of the aminoethanethiol to the dihydroxybenzene is from about 1:2 to about 4:1.

9. The method of claim 8 wherein the mole ratio is about 1:1 to about 2:1.

10. The method of claim 8 wherein n=1; $R_1$ is H or COOH; $R_2$ and $R_3$ are each H; $R_4$ and $R_5$ are each H or $C_1$–$C_4$ alkyl; and $R_6$ is H or $C_1$–$C_2$ alkyl.

11. The method of claim 10 wherein the dihydroxybenzene has the structure of formula I.

12. The method of claim 11 wherein $R_1$ is COOH, and $R_4$, $R_5$ and $R_6$ are each H.

13. The method of claim 1, 3, 5 or 7 further comprising the step of:

(c) applying to the hair following application of the aqueous system to the hair an aqueous post-treatment composition containing an oxidant.

14. The method of claim 13 wherein the post-treatment oxidant is selected from the group consisting of periodate, iodate, chlorite, acidic nitrite and persulfate salts, the oxidant being present at a concentration of from about 0.1 to about 30% by weight of the post-treatment composition.

15. The method of claim 14 wherein the oxidant is selected from the group of sodium persulfate and sodium periodate.

16. The method of claim 1, 3, or 6 wherein the aqueous system further comprises a color modifier selected from the group consisting of direct dyes, primary intermediates, couplers and mixtures thereof.

17. An aqueous hair dyeing system for permanently dyeing hair comprising tinctorially effective amounts of (a) a dihydroxybenzene having a structure:

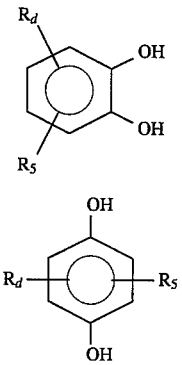

(b) an aminoethanethiol having the formula

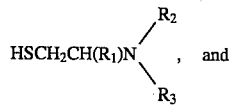

(c) a ferricyanide oxidizing agent, wherein

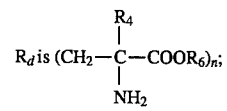

$R_1$ is H or $COOR_7$; $R_2$, $R_3$, $R_4$ and $R_5$, which may be the same or different, are H, $C_1$–$C_6$ alkyl or $C_1$–$C_6$ hydroxyalkyl; $R_6$ and $R_7$, which may be the same or different, are alkali metal, H or $C_1$–$C_6$ alkyl, and n is 1, said system having a pH of from abut 2 to about 11, the ferricyanide oxidizing agent being present in the system in at least about a stoichiometric equivalent amount relative to the dihydroxybenzene component (a).

18. The system of claim 17 wherein the dihydroxybenzene (a) and aminoethonthiol (b) are present in a hair dye composition, each such component being present at a concentration of from about 0.1 to about 10%, the mole ratio of the component (a) to the component (b) being from about 2:1 to about 1:4.

19. The system of claim 18 wherein the ferricyanide oxidizing agent is contained in the hair dye composition at a concentration of from about 0.1 to 15%.

20. The system of claim 19 wherein the ferricyanide oxidizing agent is contained in the hair dye composition in an amount of from about a stoichiometric equivalent amount to about a 50% excess over such amount.

21. The system of claim 18 wherein the ferricyanide oxidizing agent is contained in an aqueous solution having a concentration of from about 0.1 to 15%.

22. The system of claim 21 wherein the ferricyanide oxidizing agent is contained in the aqueous solution in an amount of from about a stoichiometric equivalent amount to about a 50% excess over such amount.

23. The system of claim 18 wherein the hair dye composition contains a portion of the ferricyanide oxidizing agent and wherein the remainder is present in an aqueous solution.

24. The system of claim 23 wherein the hair dye composition contains about one-half of the stoichiometric equivalent amount of the ferricyanide oxidizing agent and the aqueous solution contains the ferricyanide oxidizing agent in an amount of from about one-half of the stoichiometric equivalent amount to about a 50% excess over the total stoichiometric equivalent amount, the concentration of the ferricyanide oxidizing agent in each of the hair dye composition and the aqueous solution being from about 0.1 to about 15% by weight.

25. The system of claim 20, 22 or 24 wherein the mole ratio of dihydroxybenzene (a) to aminoethanethiol (b) is from about 1:1 to about 1:2.

26. The system of claim 20, 22 or 24 wherein the pH of the hair dye composition is from about 5 to about 9.

27. The system of claim 22 or 24 wherein the pH of the aqueous solution is from about 5 to about 9.

28. The system of claim 17, 19, 21 or 23 further comprising an aqueous post-treatment composition containing a post-treatment oxidant.

29. The system of claim 28 wherein the post-treatment oxidant is selected from the group consisting of persulfate, periodate, iodate, chlorite and acidic nitrite salts, the oxidant being present at a concentration of from about 0.1 to about 30% by weight of the post-treatment composition.

30. The system of claim 29 wherein the oxidant is sodium persulfate or sodium periodate.

31. The system of claim 17 wherein n=1; $R_1$ is H or COOH; $R_2$ and $R_3$ are each H; $R_4$ and $R_5$ are each H or $C_1$–$C_4$ alkyl, and $R_6$ is H or $C_1$–$C_2$ alkyl.

32. The system of claim 31 wherein the dihydroxybenzene has the structure of formula I.

33. The system of claim 33 wherein R, is COOH, and $R_4$, $R_5$ and $R_6$ are each H.

34. The composition of claim 17 further comprising a color modifier selected from the group consisting of direct dyes, primary intermediates, couplers, and mixtures thereof.

35. A hair dyeing kit for permanently dyeing hair having in a single package a plurality of containers, the kit comprising (a) a first container containing an aqueous hair dye composition comprising (i) about 0.1 to 10% dihydroxybenzene having a structure:

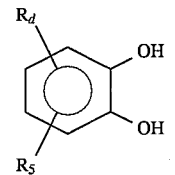

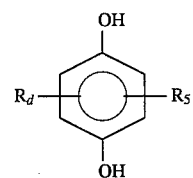

and (ii) about 0.1 to 10% of an aminoethanethiol having the formula

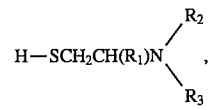

wherein

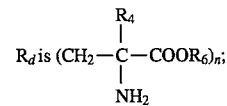

$R_1$ is H or $COOR_7$; $R_2$, $R_3$, $R_4$ and $R_5$, which may be the same or different, are H, $C_1$–$C_6$ alkyl or $C_1$–$C_6$ hydroxyalkyl; $R_6$ and $R_7$, which may be the same or different, are alkali metal, H or $C_1$–$C_6$ alkyl, and n is 1, and (b) a second container containing an aqueous solution comprising a ferricyanide oxidizing agent, a pH control agent being present in any one of said first or said second containers or in a third container, the amount of said pH control agent contained in the kit being sufficient to provide a pH of from abut 2 to 11 when the contents of the first and second containers or of the first, second and third containers are combined to form an aqueous hair dye system and the amounts of the aminoethanethiol, the dihydroxybenzene and ferricyanide oxidizing agent in the kit being sufficient to effect a permanent dyeing of hair when the contents of the containers are combined to form of the aqueous hair dye system and applied to the hair, the ferricyanide oxidizing agent being present in the system in at least about a stoichiometric equivalent amount relative to the dihydroxybenzene component (i).

36. The hair dyeing kit of claim 35 further comprising, in a container other than the container containing the ferricyanide oxidizing agent, a color modifier selected from the group consisting of direct dyes, ferricyanide intermediates, couplers, and mixtures thereof.

37. The hair dyeing kit of claim 35 wherein the pH of the aqueous system is maintained between about 5 to about 9.

38. The hair dyeing kit of claim 35 further comprising a container of an aqueous composition comprising a post-treatment oxidant.

* * * * *